United States Patent
Kydonieus et al.

(10) Patent No.: US 9,050,348 B2
(45) Date of Patent: *Jun. 9, 2015

(54) DERMAL DELIVERY DEVICE

(75) Inventors: Agis Kydonieus, Kendall Park, NJ (US); Robert G. Conway, Whitehouse Station, NJ (US); Thomas M. Rossi, Stockton, NJ (US)

(73) Assignee: Agile Therapeutics, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/463,494

(22) Filed: May 3, 2012

(65) Prior Publication Data

US 2012/0215186 A1    Aug. 23, 2012

Related U.S. Application Data

(63) Continuation of application No. 12/687,489, filed on Jan. 14, 2010, now abandoned, which is a continuation-in-part of application No. PCT/US2008/069618, filed on Jul. 10, 2008, which is a continuation-in-part of application No. PCT/US2008/069622, filed on Jul. 10, 2008.

(60) Provisional application No. 60/948,757, filed on Jul. 10, 2007, provisional application No. 60/948,759, filed on Jul. 10, 2007.

(51) Int. Cl.
| | |
|---|---|
| A61F 13/00 | (2006.01) |
| A61L 15/16 | (2006.01) |
| A61F 13/02 | (2006.01) |
| A61K 9/70 | (2006.01) |
| A61K 31/56 | (2006.01) |
| A61K 31/57 | (2006.01) |

(52) U.S. Cl.
CPC ............. *A61K 31/56* (2013.01); *A61K 9/7061* (2013.01); *A61K 9/7084* (2013.01); *A61K 31/57* (2013.01)

(58) Field of Classification Search
CPC ... A61K 9/7061; A61K 9/7084; A61K 31/56; A61K 31/57; A61K 2300/00
See application file for complete search history.

(56) References Cited

U.S. PATENT DOCUMENTS

| | | |
|---|---|---|
| 5,252,334 A | 10/1993 | Chiang et al. |
| 5,393,529 A | 2/1995 | Hoffmann et al. |
| 5,662,925 A | 9/1997 | Ebert et al. |
| 5,676,968 A | 10/1997 | Lipp et al. |
| 5,770,219 A | 6/1998 | Chiang et al. |

(Continued)

FOREIGN PATENT DOCUMENTS

WO    WO 2009/009651    1/2009

OTHER PUBLICATIONS

Minghetti et al., "Measuring adhesive performance in transdermal delivery system", American Journal of Drug Delivery, Sep. 2004, vol. 2, Issue 3.*

(Continued)

*Primary Examiner* — Isis Ghali
(74) *Attorney, Agent, or Firm* — Potter Anderson and Corroon LLP

(57) ABSTRACT

A transdermal drug delivery device is disclosed. Over an extended wear period, the device causes cumulative moderate irritation plus significant irritation of less than 5% and/or achieves a meaningful degree of detachment over a seven day period of less than 20%.

5 Claims, 1 Drawing Sheet

(56) References Cited

U.S. PATENT DOCUMENTS

| | | |
|---|---|---|
| 5,788,983 A | 8/1998 | Chien et al. |
| 5,876,746 A | 3/1999 | Jona et al. |
| 6,214,815 B1 | 4/2001 | Shangold et al. |
| 6,228,852 B1 | 5/2001 | Shaak |
| 6,660,295 B2 | 12/2003 | Watanabe et al. |
| 6,803,420 B2 | 10/2004 | Cleary et al. |
| 7,045,145 B1 | 5/2006 | Chien |
| 7,384,650 B2 | 6/2008 | Chien et al. |
| 7,576,226 B2 | 8/2009 | Tuba et al. |
| 7,855,190 B2 | 12/2010 | Bell et al. |
| 2004/0053901 A1* | 3/2004 | Chien .................. 514/171 |
| 2004/0142914 A1 | 7/2004 | Friedman et al. |
| 2005/0064031 A1 | 3/2005 | Stockemann et al. |
| 2005/0142175 A1 | 6/2005 | Langguth et al. |
| 2006/0241092 A1 | 10/2006 | Anderson et al. |
| 2007/0065495 A1 | 3/2007 | Chien |
| 2008/0025920 A1 | 1/2008 | Simes et al. |
| 2008/0069618 A1 | 3/2008 | Ishino et al. |
| 2008/0069622 A1 | 3/2008 | Sodeyama |
| 2011/0251163 A1 | 10/2011 | Rossi et al. |
| 2011/0256210 A1 | 10/2011 | Rossi et al. |
| 2012/0021041 A1 | 1/2012 | Rossi et al. |

OTHER PUBLICATIONS

International Search Report and Written Opinion, Application No. PCT/US2009/059823, mailed Dec. 9, 2009.

International Search Report and Written Opinion, Application No. PCT/US2009/059826, mailed Nov. 25, 2009.

International Search Report and Written Opinion, Application No. PCT/US2009/059828, mailed Jan. 29, 2010.

International Search Report and Written Opinion, Application No. PCT/US2010/028662, mailed May 12, 2010.

Stewart, et al., "Extended use of transdermal norelgesteromin/ethinyl estradiol: A randomized trial", Obstet. Gynecol., vol. 105, pp. 1389-1396 (2005).

U.S. Appl. No. 12/687,489, Non-Final Rejection, mailed Nov. 8, 2011.

* cited by examiner

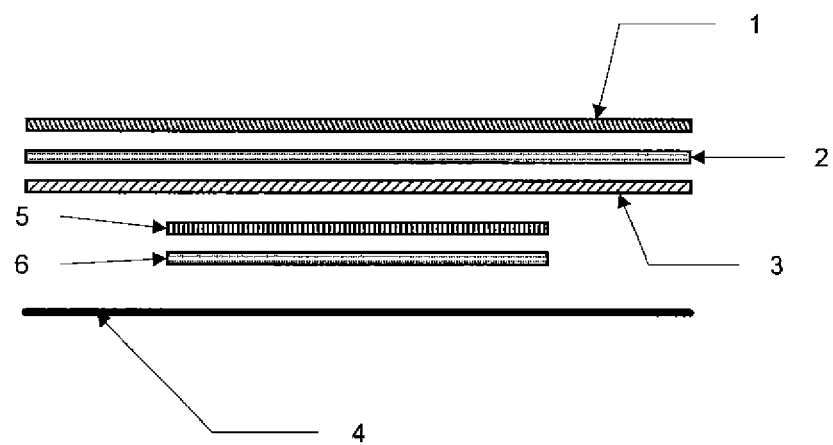

DERMAL DELIVERY DEVICE

CROSS REFERENCE TO RELATED APPLICATION

This is a continuation-in-part of U.S. Application Ser. No. PCT/US2008/069618, filed Jul. 10, 2008, which claims benefit of U.S. Provisional Application 60/948,757, filed Jul. 10, 2007, and also a continuation-in-part of U.S. Application Ser. No. PCT/US2008/069622, filed Jul. 10, 2008, which claims benefit of U.S. Provisional Application 60/948,759, filed Jul. 10, 2007, the entire contents of all of the preceding being incorporated by reference herein.

FIELD OF THE INVENTION

This invention is in the field of delivery of pharmacologically or cosmetically active agents to the skin for systemic, local, or topical administration.

BACKGROUND OF THE INVENTION

A dermal delivery device is an adhesive "patch" for application to the skin that is used to deliver a wide variety of pharmacologically and cosmetically active agents. Such patches can be used to deliver an agent transdermally, i.e., through the skin and into the bloodstream for systemic treatment or into or through the skin for local treatment. Such patches can also be used to administer topical treatments, including cosmetically active agents.

Transdermal drug delivery devices intended for extended wear, i.e., 3 or more days, are susceptible to problems of inadequate adhesion and/or skin irritation. Irritation can be caused or exacerbated by a number of factors, including the nature of the active. Certain skin permeation enhancers are also known to contribute to irritation. These include dimethyl sulfoxide (DMSO) and long chain aliphatic compounds including fatty acids, such as laurates and oleates and derivatives thereof, e.g., lauryl alcohol.

Various attempts have been made to address the skin irritation problem. These include controlling the rate of transdermal delivery of irritating drugs through use of a rate controlling membrane, inclusion of irritation inhibitors such as a lysozymal uptake inhibitor, a complexing agent, a second active agent that reduces irritation/sensitization, a sucrose fatty acid, aluminum hydroxide and/or titanium oxide. In some cases, a particular salt of an irritating active may be found to be less irritating.

SUMMARY OF THE INVENTION

This invention relates to extended wear dermal delivery devices, or patches, that cause cumulative moderate irritation plus significant irritation of less than 5%.

This invention also relates to extended wear dermal delivery devices, or patches, that achieve a meaningful degree of detachment of less than 20%.

In illustrative embodiments, the device of the invention, over a seven day wear period, causes cumulative moderate irritation plus significant irritation of less than 5% and additionally achieves a meaningful degree of detachment over a seven day period of less than 20%.

Thus, in general terms, the inventions relates to a transdermal drug delivery patch comprising (A) an active ingredient (AI) layer having a skin contacting surface and a non-skin contacting surface and comprising a pressure sensitive adhesive and the drug and (B) an elastic and porous backing material whereby at the end of an extended wear period, the patch causes cumulative moderate irritation plus significant irritation of less than 5% or causes cumulative moderate irritation plus significant irritation of less than 5% and a meaningful degree of detachment over a seven day period of less than 20%, or both.

BRIEF DESCRIPTION OF THE FIGURES

FIG. 1 illustrates an exploded cross-section of an illustrative dermal delivery system of the invention.

DETAILED DESCRIPTION OF THE INVENTION

The inventors have discovered that skin irritation, which can be a problem with extended wear patches (e.g., 3 or more days), can be minimized, and adhesion can be enhanced, by careful patch design and formulation. Through such design, use of a rate controlling membrane is unnecessary, particularly when the AI layer comprises a polymeric matrix comprising a PSA, e.g., as described below. It may also not be necessary to employ irritation inhibitors or to employ particular salt forms selected on the basis of reduced irritancy.

It may also be possible to employ skin permeation enhancers that are known to be skin irritants because removal of other sources of irritation, e.g., physical stress on the skin, are minimized. Such permeation enhancers include, e.g., dimethyl sulfoxide (DMSO) and long chain aliphatic compounds such as fatty acids or esters or derivative of fatty acids, e.g., $C_8$-$C_{20}$ saturated or unsaturated fatty acids such as lauryl lactate and isopropyl myristate. These include, e.g., $C_8$-$C_{20}$ saturated or unsaturated fatty alcohols, such as myristyl, palmityl or oleyl alcohols.

Thus, in illustrative embodiments of the invention, patches do not comprise a skin irritation inhibitor, do not employ a rate-controlling membrane, do not employ a non-irritating salt of an irritating active, and/or do not require a supporting layer for the AI layer that is flexible and porous. It is also not necessary to employ an adhesion adjusting agent, such as polydiorganosiloxane polymer in order to reduce tissue damage upon removal of the patch.

In an illustrative embodiment of the invention, the patch is intended for application to normal healthy skin, such as on the arm, chest, back, buttocks or leg, although other embodiments can be designed for use on inflamed or irritated skin tissue. In illustrative embodiments, the release and transdermal administration are dependent on drug concentration in the AI layer.

For example, designing and formulating a patch that adheres well can reduce irritation from physical stresses on the skin such as by minimizing friction caused by movement of the patch against the skin; use of materials that are elastic such that they conform by stretching and re-forming (i.e., recovering more or less its original dimensions after being stretched during wear) can improve adhesion and minimize irritation by improving adhesion and/or by minimizing the friction between the patch and the skin; use of materials that are soft such that they do not have "hard" edges can minimize irritation such as by reducing friction between the edges of the patch or of its components, e.g., an overlay, and the skin; use of a humectant such as PVP can improve adhesion and reduce irritation such as by minimizing buildup of moisture between the patch or its components and the skin; use of a backing material that is porous (i.e., water vapor-permeable to the extent that moisture that does build up in the AI layer or in the extended perimeter of an overlay can escape) can improve adhesion by preventing buildup of moisture and also thereby reduce irritation.

A covering that is attached directly or indirectly to the AI layer, e.g., an overlay can comprise an elastic and porous material adjacent the non-skin-contacting surface of the AI layer. By "elastic" is meant that the material is capable of stretching with skin movement during normal activities and of re-forming substantially to its original shape and size. By "porous" is meant that the material is permeable, i.e., permeable to moisture, more specifically, permeable to water vapor. The elasticity and porosity of such backing material are such that, at the end of an extended, e.g., seven day, wear period, the patch causes cumulative moderate irritation plus significant irritation of less than 5%, including 4% or less, 3% or less, and 2% or less and/or such that there is a meaningful degree of detachment over a seven day period of less than 20%.

Preferably, such elastomeric and permeable layer is part of an overlay that extends beyond the perimeter of the AI layer. In this case, an internal backing layer that comprises a non-porous material covering all or a portion of the non-skin contacting surface of the active ingredient layer can be used to prevent or minimize passage of the components of the polymer matrix in the AI layer through the non-skin-contacting surface of the device. In this embodiment, the elastic and porous backing material in the overlay provides sufficient elasticity and permeability to the device to confer adequate adhesion and acceptable irritation, i.e., moderate irritation plus significant irritation of <5% including 4% or less, 3% or less, and 2% or less.

In a particular illustrative embodiment, an impermeable internal backing layer is adhered to the entire surface area of the non-skin contacting face of the active ingredient layer. In such embodiment, a peripheral adhesive system such as an overlay is employed to improve adhesion and reduce irritation, particularly by proper choice of a PSA and overlay material. Polyisobutylene (PIB) PSAs, such as are described below, are particularly useful in the PSA layer of the overlay. Other useful materials for the overlay include materials that are flexible, including multidimensionally elastically stretchable films or fabrics. Such elastomeric and soft materials include porous foams and woven or nonwoven fabrics, which will stretch and reform with movement of the skin, retain their shape and reduce buildup of moisture between the peripheral adhesive layer and the skin. The porosity of the material can be chosen such that the water vapor permeation rate through the material is higher than the transepidermal water loss.

When PSAs that are of low molecular weight such that they would pass through the permeable, i.e., porous, overlay covering, e.g., a PIB, are employed in the overlay, it can be useful also to employ an intermediate layer that permits moisture, but not the PSA, to reach and penetrate the porous material. Such intermediate layer, which need not detract from the elasticity of the backing layer, can be, e.g., a polyacrylate PSA or a polyurethane. In addition, if the PSA is hydrophobic, such as a PIB PSA, it is advantageous to employ a humectant, such as PVP, in the PSA layer of the overlay.

As noted above and discussed below, the overlay can extend beyond the perimeter of the AI layer in all directions, typically by a margin of about 0.1 to about 1.5 cm, more specifically about 0.3 to about 1.2 cm and more specifically about 0.8 cm beyond the perimeter of the AI layer. The precise surface area of extension is selected to provide a peripheral adhesive surface area that is adequate to ensure good adhesion throughout the contemplated wear period but that is not larger than necessary. Use of an overlay that is larger than necessary has several disadvantages, e.g., a larger skin contact surface area can increase irritation and is generally more noticeable and therefore less aesthetically pleasing; in some embodiments, a patch surface area, including a peripheral adhesive, can be less than about 50 $cm^2$, less than about 30 $cm^2$, or less than about 25 $cm^2$.

Such patch design also preferably incorporates a humectant into the polymeric matrix of the AI layer. As mentioned above and further described below, the humectant absorbs moisture from the surface of the skin and thereby reduces irritation and enhances adhesion.

Patches designed as described above and as illustrated hereinbelow, at the end of an extended, e.g., seven day, wear period, can cause cumulative moderate irritation plus significant irritation of less than 5%, including 4% or less, 3% or less, and 2% and/or can achieve a meaningful degree of detachment over a seven day period of less than 20%, including less than 18%, less than 15%, less than 12%, and less than 10%.

By "moderate irritation plus significant irritation" is meant that the patch causes erythema, papules, definite edema, vesicular eruption, with the reaction spreading beyond test (i.e., application) site. With reference to the FDA's draft Guidance on Ethinyl Estradiol; Norelgestromin extended release/transdermal film, July 2009 ("FDA Guidance"), a copy of which is incorporated herein as though fully set forth, "moderate irritation plus significant irritation" corresponds to a Dermal Response/Skin Appearance score of 7.

A cumulative moderate irritation plus significant irritation of less than 5% means that moderate irritation plus significant irritation was observed in fewer than 5% of skin application sites on patients in a study population of, e.g., about 50 to about 1000 patients, e.g., about 100 to about 300 patients, including 200 patients which is the number of patients recommended in the FDA Guidance.

By "meaningful degree of detachment" is meant that a patch is less than 50% adhered, i.e., more than half of the patch has become detached from the skin. With reference to the FDA Guidance, "meaningful degree of detachment" corresponds to an Adhesion score of 3 or 4.

A meaningful degree of detachment over a seven day period of less than 20%, means that there was a meaningful degree of detachment in fewer than 20% of patients in a study population of, e.g., 10 to 1000 patients.

A mean adhesion score means the mean (p<0.05) adhesion score in a population of patients (n=100 to 500) using the following adhesion scoring patch:

0=>/=90% adhered (essentially no lift off the skin)
1=>/=75% to <90% adhered (some edges only lifting off the skin)
2=>/=50% to 75% adhered (less than half of the patch lifting off the skin)
3=>0% to <50% adhered but not detached (more than half of the patch lifting off the skin without falling off)
4=0% adhered—patch detached (patch completely off the skin).

In illustrative embodiments of the invention, the patch achieves both, a cumulative moderate irritation plus significant irritation of less than 5% and a meaningful degree of detachment over a seven day period of less than 20%.

In certain illustrative embodiments, the overlay can be packaged separately from the AI layer. An internal backing layer can be integrated with the AI layer or with the overlay. In either case, the user would apply the overlay on top of the AI layer, rather than applying an integrated patch that comprises both the overlay and the AI layer.

The description that follows is of an illustrative embodiment of the invention for dermal delivery of a composition comprising contraceptive hormones and that comprises one or more volatile components. Of course, the active can be any drug that is active when administered by transdermal delivery, passive or otherwise. Furthermore, while use of a seal between an overlay and a release liner to minimize or prevent loss of volatile components, as described hereinbelow, can be advantageous, such seal is not an essential feature of the current invention which is more broadly directed at achieving adequate adhesion and acceptable skin irritation.

With reference to FIG. 1, this illustrative device of the invention comprises 4 layers. One is the AI layer (6). The second is a release liner (4). The third is an internal backing layer (5). The fourth is an overlay, which in this illustrative device, itself comprises three component layers (1,2,3), referred to herein below as, respectively, a PSA layer (3), an intermediate layer (2), and an overlay covering or overlay coating (1). The overlay can also be described as comprising, in this illustrative embodiment, a PSA layer (3) and an overlay covering (1 and 2). In any event, one feature of this illustrative embodiment of the invention is formation of a seal between the PSA layer (3) of the overlay (1,2,3) and the release liner (4).

A feature of a related aspect of this illustrative embodiment of the invention is use of a PIB PSA in the PSA layer (3) of the overlay (1,2,3).

A feature of another related aspect of this illustrative embodiment of the invention is use of an overlay (1,2,3) comprising a PIB PSA layer (3) and a material (1,2) that covers the PIB PSA layer, so that the PIB PSA does not come into contact with fingers or clothing, but that permits water vapor transmission outward from the skin. As illustrated in FIG. 1, the material comprises Layers 1 and 2, Layer 2 being a PSA that prevents migration of the PIB PSA into the overlay coating (1).

A feature of another aspect of this illustrative embodiment of the invention is use of an intermediate layer (2) between the PIB PSA layer (3) and a porous overlay covering (1).

In illustrative embodiments, the entire patch is flexible so that it will adhere effectively and comfortably to the contours of the site of application and so that it will withstand the flexions associated with normal living activities.

These and other aspects of the invention are more fully described hereinbelow or otherwise will be apparent to a person of ordinary skill in the art based on such description.

An illustrative, non-limiting, embodiment of the invention that comprises an entire transdermal delivery system of the invention is as follows.

The AI Layer

Layer 6 comprises the AI and a volatile component, typically in a PSA matrix. The volatile component is typically at least partially dissolved in the AI layer. So, for example, in an illustrative embodiment of the invention, Layer 6 comprises one or more hormones as AIs, an acrylic PSA, and a volatile skin permeation enhancer. The volatile component, however, can also be, for example, the AI itself or a solvent or carrier. Illustrative formulations of transdermal hormone compositions useful in delivery devices of the present invention are described, for example, in U.S. Pat. No. 7,045,145 and in US 20070065495.

In an illustrative embodiment, the AI is an active pharmaceutical ingredient (API) that is one or more hormones such as a progestin, e.g., levonorgestrel, and an estrogen, e.g., ethinyl estradiol or 17-β estradiol, dispersed in an adhesive polymer matrix. In another aspect of the invention for delivery of a hormone, the API is limited only to a progestin. In other such aspects, the API comprises a progestin, an estrogen and a testosterone, or a testosterone alone.

Other APIs that can also be delivered in accordance with this invention include "small molecules", i.e., low molecular weight (e.g., <2000 Daltons) synthetic organic compounds such as but not limited to fentanyl, nicotine, scopolamine, nitroglycerine, clonidine, methylphenidate, lidocaine, prilocaine, oxybutynin, antipsychotics such as fluphenazine, alprazolam, risperidone, and olanzapine, Parkinsons drugs such as rotigotine and selegilene Alzheimer's drugs such as rivastigmine and donepezil, anti-hypertensives such as enalapril, BPH drugs such as tamsulosin and terazosin, and anti-asthma drugs such as albuterol and montelukast.

The AI can also be a cosmetic agent such as keratolytic agents such as alpha- and beta-hydroxycarboxylic acids and beta-ketocarboxylic acids; alpha-hydroxy acids such as glycolic acid, lactic acid, tartaric acid, malic acid, citric acid, mandelic acid and, in general, fruit acids; beta-hydroxy acids such as salicylic acid and its derivatives; antibacterials such as clindamicyn or erythromycin phosphate, or antibiotics of the tetracycline type; ascorbic acid and its biologically compatible salts and esters; enzymes; tautening agents such as protein, soya and wheat powders; hydroxylated polyacids; sucroses and their derivatives; urea; amino acids; plant and yeast extracts; protein hydrolysates such as collagen and elastin hydrolysates; hyaluronic acid; mucopolysaccharides; vitamins; panthenol; folic acid; acetylsalicylic acid; allantoin; kojic acid; hydroquinone; retinoic acid and derivatives thereof; fatty acids; etc.

As described in US 20070065495, an illustrative Layer 6 is prepared as described in Example 1, below. This example describes formulations that use a combination of skin permeation enhancers, including DMSO and a lower (C1-C4) alkyl ester of lactic acid such as ethyl lactate, both of which are volatile components and are examples of volatile components that may be included in a transdermal drug delivery device of the invention. By "volatile," is meant that the agent has a vapor pressure above 0.1 mm Hg at 20 C. Other illustrative volatile components useful in the present invention are known to those skilled in the art and include other volatile organic solvents, for example, sulfoxides such as decyl methyl sulfoxide; alcohols such as ethanol, propanols, hexanols, and benzyl alcohol, fatty acids such as valeric acid, isovaleric acid, isopropyl butyrate, ethyl acetate, and butyl acetate; polyols such as butanediol and ethylene glycol; amides such as dimethylacetamide, diethyl toluamide, dimethylformamide, pyrrolidone, and methylpyrrolidone; terpenes such as limonene, pinene, terpinone, mentone, eucalyptus, and menthol; alkanes such as hexane and heptane, and organic acids such as citric acid.

Skin permeation enhancers and solvents additional to DMSO and similar organic solvents include but are not limited to those described in Example 1.

The following description relates to a preferred formulation of Layer 6 for delivery of a hormone, said layer, or patch, comprising one or more hormones, skin permeation enhancers, and a PSA matrix comprising an adhesive polymer and a humectant/plasticizer.

Skin Permeation Enhancers: Drug molecules released from a transdermal delivery system must be capable of penetrating each layer of skin. In order to increase the rate of permeation of drug molecules, a transdermal drug delivery system, desirably, is able to increase the permeability of the outermost layer of skin, the stratum corneum, which provides the most resistance to the penetration of molecules. In this regard, the present invention allows for a transdermal drug delivery system that employs one or more skin permeation enhancers in specific amounts.

A combination of skin permeation enhancing agents is preferably employed in the practice of the present invention for delivery of levonorgestrel and ethinyl estradiol (EE) or 17 beta-estradiol. The combination comprises a mixture of (1) a pharmaceutically acceptable organic solvent, such as dimethyl sulfoxide (DMSO), (2) a fatty (C8-C20) alcohol ester of a hydroxy acid, such as lauryl lactate, (3) a lower (C1-C4) alkyl ester of a hydroxy acid, e.g., ethyl lactate, and (4) a C6-C18 fatty acid, such as capric acid. In specific embodiments, the fatty alcohol ester of lactic acid is lauryl lactate and the lower alkyl ester of lactic acid is ethyl lactate. A medium-to long-chain fatty acid in the skin permeation enhancer formulation can be employed among the skin permeation enhancers. Capric acid is preferred for use but other C6-C18 saturated or unsaturated fatty acids may be used, including but not limited to caproic acid, caprytic acid, lauric acid and myristic acid, to name a few.

These skin permeation enhancers can be present in amounts as described below. In certain embodiments, one or more of the skin permeation enhancers may be eliminated from the polymer matrix.

In a particular such embodiment, the pharmaceutically acceptable organic solvent is DMSO. Other organic solvents suitable for use in the present invention include, but are not limited to, C1-C8 branched or unbranched alcohols, such as ethanol, propanol, isopropanol, butanol, isobutanol, and the like, as well as azone (laurocapram: 1-dodecylhexahydro-2H-azepin-2-one) and methylsulfonylmethane, to name a few.

The fatty alcohol ester of a hydroxy acid can be a fatty alcohol ester of lactic acid, such as lauryl lactate. However, other hydroxy acids and fatty alcohols may be utilized. Alternative hydroxy acids include, but are not limited to, alpha-hydroxy acids such as glycolic acid, tartaric acid, citric acid, malic acid and mandelic acid, as well as the beta-hydroxy acid, salicylic acid. Alternative fatty alcohols include any C8-C20 saturated or unsaturated fatty alcohols, such as myristyl, palmityl or oleyl alcohols, to name a few.

The lower alkyl ester of hydroxy acid can also utilize lactic acid, and can be, e.g., ethyl lactate. However, other hydroxy acids, such as glycolic acid, tartaric acid, citric acid, malic acid, mandelic acid and salicylic acid, may also be utilized. In addition isopropylmyristic acid (IPM) may be used as a substitute for the lower alkyl ester of hydroxy acid.

The aforementioned combination of skin permeation enhancers may be used to enhance transdermal delivery of steroid hormones from any type of transdermal delivery device. An adhesive polymer matrix-type system as described in detail herein is preferred for use; however, the enhancer combination may also be utilized in non-adhesive polymers, as well as in multi-layer or reservoir-type transdermal delivery systems, to name a few.

Hormones: A transdermal drug delivery device utilizing the aforementioned skin permeation enhancers can be used to deliver various types of API, including a hormone, capable of transdermal delivery. In one embodiment, a combination of a progestin and an estrogen is utilized for one or more of the following purposes: (1) control of fertility, (2) control of acne, (3) treatment of endometriosis, (4) treatment of premenstrual dysphoric disorder (PMDD), and (5) induction of amennorhea. In another embodiment, a progestin alone is utilized for one or more of the following purposes: (1) control of fertility, (2) supporting pregnancy, (3) as an alternative hormonal therapy for individuals for whom estrogen is contraindicated (e.g., lactating females), and (4) preventing galactorrhea. In still another embodiment, a combination of progestin, estrogen and testosterone is utilized as a hormone replacement therapy for the treatment of deficiency of these hormones in females. Yet another embodiment is directed to a THDS formulated for delivery of testosterone alone, which is useful for the treatment of decreased libido resulting from testosterone deficiency in both males and females.

Levonorgestrel is a potent progestin on a weight-dose basis, which is an important factor since the progestins often exhibit a much lesser degree of transdermal absorption than do the estrogens. Other progestins that could be used in part or total are norgestrel, norgestimate, desogestrel, gestodene, norethindrone, nore-thynodrel, hydrogesterone, ethynodiol dicetate, hydroxyprogesterone caproate, medroxyprogesterone acetate, norethindrone acetate, progesterone, megestrol acetate, gestogen and certain others which are biocompatible and absorbable transdermally. These include biocompatible derivatives of progestins that are transdermally absorbed, some of which, advantageously, are bioconvertible after transdermal absorption to the original progestin. The progestin and other hormones selected preferably have high compatibility with each other.

For combinations of progestin with estrogen, the synthetic hormone ethinyl estradiol is particularly suitable, although natural estrogen or other analogs can be used. This hormone may be transdermally delivered in conjunction with the particularly suitable progestin, levonorgestrel, by a TDHS of the present invention at desirable daily rates for both hormones. Ethinyl estradiol and levonorgestrel are compatible and can be dispersed in the adhesive polymer formulation. Typically, a transdermal dosage unit designed for one-week therapy should deliver at least about 20 μg/day of levonorgestrel, e.g., about 50 to about 100 μg/day (or an equivalent effective amount of another progestin) and 10-50 μg/day of ethinyl estradiol (or an equivalent effective amount of another estrogen). Those respective amounts of progestin and estrogen are believed to be necessary to inhibit ovulation and to maintain normal female physiology and characteristics. In the present invention, the amount of levonorgestrel transdermally delivered is preferably 30 μg per day for more than one day to about one week with a 15 cm$^2$ transdermal delivery device.

Derivatives of 17 β-estradiol that are biocompatible, capable of being absorbed transdermally and preferably bioconvertible to 17 β-estradiol may also be used, if the amount of absorption meets the required daily dose of the estrogen component and if the hormone components are compatible. Such derivatives of estradiol include esters, either mono- or di-esters. The monoesters can be either 3- or 17-esters. The estradiol esters can be, illustratively speaking, estradiol-3,17-diacetate; estradiol-3-acetate; estradiol 17-acetate; estradiol-3,17-divalerate; estradiol-3-valerate; estradiol-17-valerate; 3-mono-, 17-mono- and 3,17-dipivilate esters; 3-mono-, 17-mono- and 3,17-dipropionate esters; 3-mono-, 17-mono- and 3,17-dicyclo pentyl-propionate esters; corresponding cypionate, heptanoate, benzoate and the like esters; ethinyl estradiol; estrone; and other estrogenic steroids and derivatives thereof that are transdermally absorbable.

Combinations of the above with estradiol itself (for example, a combination of estradiol and estradiol-17-valerate or further a combination of estradiol-17-valerate and estradiol-3,17-divalerate) can be used with beneficial results. For example, 15-80% of each compound based on the total weight of the estrogenic steroid component can be used to obtain the desired result. Other combinations can also be used to obtain desired absorption and levels of 17 β-estradiol in the body of the subject being treated.

Formulations comprising testosterone may utilize natural testosterone or synthetic testosterones that are absorbed transdermally. For instance, methyl testosterone is suitable for use in the present invention. A transdermal device for testosterone delivery in premenopausal women should be formulated for delivery of up to about 300 ug daily. For treatment of testosterone deficiency in males, transdermal hormone delivery systems should be formulated to deliver up to about 3-6 mg daily.

It will be appreciated that the hormones may be employed not only in the form of the pure chemical compounds, but also in a mixture with other pharmaceuticals that may be transdermally applied or with other ingredients which are not incompatible with the desired objective as listed above. Thus, simple pharmacologically acceptable derivatives of the hormones such as ethers, esters, amides, acetals, salts and the like, if appropriate, may be used. In some cases, such derivatives may be preferred. The progestin compound and the estrogenic steroid are ordinarily dispersed or dissolved concurrently in fabricating the hormone-containing adhesive polymer matrix or they may be dispersed or dissolved separately.

As noted above, this invention is not limited to transdermal delivery of an estrogen or a progestin or even to transdermal delivery of a steroidal hormone. Instead, the invention can be practiced using a wide range of actives.

Polymers Used as Active Patch Components: The AI-containing layer can be a polymer matrix comprising the pharmaceutically or cosmetically active ingredient. The polymer can be a PSA to form a biologically acceptable adhesive polymer matrix, preferably capable of forming thin films or coatings through which the AI can pass at a controlled rate. Suitable polymers are biologically and pharmaceutically compatible, nonallergenic, insoluble in and compatible with body fluids or tissues with which the device is contacted. The use of water soluble polymers is generally less preferred since dissolution or erosion of the matrix would affect the release rate of the AI as well as the capability of the dosage unit to remain in place on the skin. So, in certain embodiments, the polymer is non-water soluble.

Preferably, polymers used to form a polymer matrix in the AI-containing layer have glass transition temperatures below room temperature. The polymers are preferably non-crystalline but may have some crystallinity if necessary for the development of other desired properties. Cross-linking monomeric units or sites can be incorporated into such polymers. For example, cross-linking monomers that can be incorporated into polyacrylate polymers include polymethacrylic esters of polyols such as butylene diacrylate and dimethacrylate, trimethylol propane trimethacrylate and the like. Other monomers that provide such sites include allyl acrylate, allyl methacrylate, diallyl maleate and the like.

A useful adhesive polymer formulation comprises a polyacrylate adhesive polymer of the general formula (I):

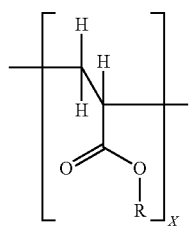

wherein X represents the number of repeating units sufficient to provide the desired properties in the adhesive polymer and R is H or a lower (C1-C10) alkyl, such as ethyl, butyl, 2-ethylhexyl, octyl, decyl and the like. More specifically, it is preferred that the adhesive polymer matrix comprises a polyacrylate adhesive copolymer having a 2-ethylhexyl acrylate monomer and approximately 50-60% w/w of vinyl acetate as a co-monomer. An example of a suitable polyacrylate adhesive copolymer for use in the present invention includes, but is not limited to, that sold under the tradename of Duro Tak® 87-4098 by National Starch and Chemical Co., Bridgewater, N.J., which comprises a certain percentage of vinyl acetate co-monomer.

Humectant/plasticizer: Preferably, a plasticizer/humectant is dispersed within the adhesive polymer formulation. Incorporation of a humectant in the formulation allows the dosage unit to absorb moisture from the surface of skin which in turn helps to reduce skin irritation and to prevent the adhesive polymer matrix of the delivery system from failing. The plasticizer/humectant may be a conventional plasticizer used in the pharmaceutical industry, for example, polyvinyl pyrrolidone (PVP). In particular, PVP/vinyl acetate (PVPNA) co-polymers, such as those having a molecular weight of from about 50,000, are suitable for use in the present invention. The PVPNA acts as both a plasticizer, acting, to control the rigidity of the polymer matrix, as well as a humectant, acting to regulate moisture content of the matrix. The PVP/VA can be, for example, PVPNA S-630 which is a 60:40 PVP:VA co-polymer that has a molecular weight of 51,000 and a glass transition temperature of 110 C. The amount of humectant/plasticizer is directly related to the duration of adhesion of the overlay. Preferably, the PVP/vinyl acetate is PVP/VA S-630 supplied by International Specialty Products, Inc. (ISP) of Wayne, N.J., wherein the PVP and the vinyl acetate are each present in approximately equal weight percent.

The shape of the device of the invention is not critical. For example, it can be circular, i.e., a disc, or it can be polygonal, e.g., rectangular, or elliptical. The surface area of the AI layer generally should not exceed about 60 cm$^2$ in area. Preferably, it will be about 5 to 50 cm$^2$, more preferably, about 8 to about 40 cm$^2$. Most preferably, the discs will be about 10 to about 20 cm$^2$. A disc of 15 cm$^2$ is preferred because of its relatively small size, yet being capable of dispersing high levels of hormones. Specific embodiments of the invention feature patches having an AI layer with a surface area of 10, 12.5, 15, 17.5 or 20 cm$^2$. However, other sizes may be utilized.

In illustrative embodiments, the AI layer is disposed directly between the internal backing layer and the release liner. There is not a "reservoir" or pre-formed pocket, as such; rather, the AI layer and internal backing layer are hermetically sealed between the overlay and the release liner.

With such polymeric matrix, the active ingredient does not need to be contained, e.g., in microcapsules or other containment/release means.

The Internal Backing Layer

When the PSA comprises a polyacrylate matrix, as described above, the organic component can escape through the skin and non-skin contacting surface of the system. In order to minimize such escape through non-skin contacting surface, an internal backing layer can be employed. This layer, which inhibits absorption of components of the AI layer into the overlay, is illustrated as Layer 5 in FIG. 1.

Such internal backing layer can be made of any suitable material that is impermeable or substantially impermeable to the AI and to excipients of the adhesive polymer matrix. The internal backing layer serves as a protective cover for the AI layer and provides a support function. The backing layer can be formed so that it is essentially the same size as the hormone-containing adhesive polymer matrix or it can be of larger dimension so that it can extend beyond the edges of the AI-containing patch outwardly. The backing layer can be any appropriate thickness that will provide the desired protective and support functions. A suitable thickness is from about 10 to about 300 microns. More specifically, the thickness is less than about 150 microns, yet more specifically, it is less than about 100 microns, and most specifically, the thickness is less than about 50 microns.

Examples of materials suitable for making the internal backing layer are films of polypropylene, polyesters such as poly(ethylene terephthalate), metal foils, metal foil laminates of such suitable polymer films, and the like. Polyester films, such as Mylar® (DuPont Teijin) and Scotchpak® 9732 (3M Company), are particularly suitable for use in the present invention.

The internal backing layer is, in general, a separate layer from the overlay or any component layer of the overlay, e.g., it is not co-extruded or co-molded with the overlay. In illustrative embodiments, the internal backing layer can be coated on the surface adjacent the AI layer with a "tie-coat," e.g., a polyvinyl acetate-polyethylene vinyl acetate copolymer or other soft polymer or copolymer.

The Release Liner

The surface area of the release liner is greater than that of the AI layer. This can be seen in FIG. 1, where the diameter (in the case of a round device) or width and length (in the case of a polygonal device) of Layer 3 is greater than that of Layers 5 and 6, such that it extends beyond the AI layer in some or all directions.

The release liner is made of any material (1) that is impermeable or substantially impermeable to the components of the AI layer, (2) to which the PSA in the overlay will adhere, as discussed further hereinbelow, and (3) that is readily removable by peeling from the AI layer and overlay PSA just prior to applying to the skin. "Impermeable" and "substantially impermeable," will be understood to mean that the components of the AI layer, in particular, the volatile components, do not become absorbed by or otherwise pass into or through the release liner such as to alter the performance of the device, in particular, the skin permeability or efficacy of the active ingredients.

The release liner can have the same dimensions as the overlay, discussed below, or it can extend totally or partially beyond the edge of the patch. In one illustrative embodiment, the release liner extends partially beyond the overlay so as to form "tabs" of release liner material that extend beyond the edges of the overlay for easy separation of the release liner from the rest of the system.

Preferably, it comprises a fluorinated or siliconized polyester film or another fluorinated or siliconized polymer such as a polyacrylonitrile copolymer, or a foil lined with a siliconized or fluorinated polymer. The release liner is preferably not polystyrene because it has been shown that polystyrene will absorb DMSO. A preferred material for the release liner when the layer 4a of the overlay comprises a PTB PSA is a Scotchpak® liner (3M Company), such as Scotchpak® 1022 or Scotchpak® 9744 fluorinated polyester release liners.

In this illustrative embodiment, a drug-permeable membrane, rate-control membrane, porous membrane, seal peel, peelable disk or other layer, covering or coating between the polymeric matrix and the release liner is not required. Instead, in illustrative embodiments, owing to the viscosity of the polymeric matrix, the release liner is in direct contact with the AI layer and, outside the perimeter of the AI layer, with the overlay.

The Overlay

The overlay in this illustrative embodiment comprises three component layers, referred to in FIG. 1 as layers 1, 2, and 3. The overlay comprises a PSA in which the solubility of the volatile components is less, preferably significantly less, than the solubility of those same components in the AI matrix. So, e.g., when the volatile component is DMSO or ethyl lactate, a PIB PSA may be chosen. With reference to FIG. 1, the PIB PSA layer is Layer 3. Generally, such FIB PSA comprises a mix of a low to medium molecular weight and a high molecular weight PIB, a plasticizer such as polybutene, and a hydrocolloid such as a cross-linked polyvinylpyrrolidine. Useful PIBs include, e.g., Oppanol® PIBs (BASF), which have average molecular weights of between 40,000 and 4,000,000.

A useful PIB PSA comprises crospovidone such as Kollidon® CLM crospovidone (BASF) (e.g., 5-45 wt %, preferably 15-30 wt %, and more preferably 20-25 wt %); a low viscosity PIB such as Oppanol® B12 (molecular weight: 51000, viscosity at 150 C: 150 Pascal-seconds) (e.g., 10-60 wt %, preferably 30-50 wt %); a high viscosity PIB such as Oppanol® B100 (viscosity: approximately 1100 Pascal-seconds) (e.g., 2-15 wt %, preferably 5-15 wt %); a polybutene such as Indopol® 1900 (Innovene LLC) (molecular weight: 2500, viscosity at 100 C: 3900-4200 centistokes) (e.g., 10-60 wt %, preferably 20-40 wt %); and a mineral oil (0-20 wt %). For example, an illustrative formulation comprises about 20 wt % crospovidone, about 40 wt % of a low viscosity PIB, about 8 wt % of a high viscosity PIB and about 32 wt % of polybutene. (The term, "about," as used in this specification, means plus or minus 10%. By "low viscosity" is meant less than about 300 Pascal-seconds and by "high viscosity" is meant more than about 800 Pascal-seconds, when the viscosity is measured at 150 C.) Cross-linking of the PVP is useful because such cross-linked polymers tend to be water-swellable but water insoluble. Such PIB PSA can provide good wear stability, e.g., attachment under normal living conditions for at least 7 days.

Other rubber-based polymers that can be used in place of PIB PSA in the overlay include silicone-based PSAs, such as BIO-PSA® (Dow Corning); copolymers and terpolymers of styrene/butadiene/styrene, styrene/isoprene/styrene, and styrene-ethylene/butylenes-styrene, such as Kraton D styrene/butadiene and Kraton G styrene-ethylene/butylene-styrene or styrene-ethylene/propylene-styrene. Isoprene rubbers, such as Kraton IR linear polyisoprene homopolymers, can also be used.

As shown in FIG. 1, and like the release liner, the overlay can extend beyond the perimeter of the AI layer in all directions, typically by a margin of about 0.1 to about 1.5 cm, more specifically about 0.3 to about 1.2 cm, and yet more specifically about 0.8 cm beyond the perimeter of the AI layer.

The overlay, if it comprises a PSA layer, improves adherence to the skin by supplementing the adhesion provided by the PSA in the AI layer, if present, or, in the case of an AI layer that does not comprise a PSA, it provides adherence to the skin.

In addition, in one illustrative embodiment of the invention, the overlay adheres to the release liner around the perimeter of both layers, thereby sealing in the components of the AI layer. By properly selecting the materials that comprise the overlay and the release liner, this seal between them prevents, or substantially prevents, escape of the volatile component in the AI layer but still allows the release liner to be peeled away easily by the user prior to topical application.

The seal is formed in situ by mechanically pressing together the edges of the overlay that extend beyond the perimeter of the AI layer and the edges of the release liner that extend beyond the perimeter of the AI layer. When the first overlay layer is a PIB PSA and the release liner is a fluorinated or siliconized polyester film, a suitable seal can be made by applying pressure. The amount of pressure required to form such seal is not critical. Finger pressure is adequate. Of course, in an illustrative embodiment of the invention, it is desirable that the seal can be broken by peeling the release liner from the rest of the system by hand just prior to application to the skin.

The seal between the overlay PSA and the release liner prevents, or substantially prevents, loss of the components of the AI layer through the seal between these two layers such as during storage of the system.

The seal can also be formed by ultrasonically welding the release liner to the overlay or to the internal backing layer such as is described in the U.S. patent application based on WO2009009651, which is incorporated in its entirety herein as though fully set forth.

The overlay can also comprise a covering (1) that does not comprise a PSA, i.e., that comprises a non-PSA layer, such that the surface of the overlay that is exposed to fingers, clothing and ambient dirt or dust is non-tacky, is flexible or malleable so as to flex with skin and muscle movements, is of an unnoticeable or attractive color and texture, and permits moisture from the skin to pass through the device owing to its being porous or otherwise permeable to water.

Thus, it may be desirable to utilize a multi-layered overlay comprising a first layer of a PSA in which the volatile component is insoluble, covered with an intermediate layer and an overlay covering having the properties described above. Such illustrative overlay is illustrated in FIG. 1 as Layers 1, 2, and 3.

While a PIB PSA is useful for containing DMSO or ethyl lactate, or both, in the AI layer, the PIB PSA may flow through most overlay coverings having the properties described above. Such flow of the PIB PSA can cause the device to become tacky and discolored. Therefore, it may be desirable to use an overlay covering that itself comprises two layers, one of which is a polymeric layer interposed between the PIB PSA (an intermediate layer) and a backing layer. Such intermediate layer can be a polyacrylate PSA as described above, because such PSA will substantially prevent flow of the PIB PSA into and through the overlay covering but will substantially not itself migrate into or through the overlay covering.

Thus, in an illustrative embodiment of the invention, the AI layer comprises a polyacrylate matrix further comprising a humectant, e.g., PVP/VA, and skin permeation enhancers including DMSO, ethyl lactate, or both, or another one or more volatile organic solvents; the overlay is a laminate that comprises three layers: a PIB PSA layer (3, in FIG. 1); an intermediate layer that comprises a material that does not permit flow of the PIB PSA but that does permit passage of moisture (2, in FIG. 1); and an overlay covering (or backing layer) that is non-tacky, attractive, flexible, and moisture permeable (1, in FIG. 1).

Materials useful in the intermediate layer include, e.g., polyacrylates, polyurethanes, plasticized polyvinyl chlorides, and copolymers of polyethylene and ethyl vinyl acetate. Rubber-based polymers that are of very high molecular weight, e.g., at least about 150,000 Daltons can also be used, as can rubber-based polymers that can be crosslinked. Examples include the Kraton D styrene/butadiene, Kraton G styrene-ethylene/butylene-styrene or styrene-ethylene/propylene-styrene and Kraton IR linear polyisoprene homopolymers Butyl rubbers and silicone rubbers, which are crosslinkable, can also be used. The intermediate layer can comprise a PSA that binds the first overlay layer as well as the overlay covering. High molecular weight, cross-linked polymers are preferred. Preferably, such PSA is a polyacrylate such as is described above with reference to the AI layer.

Materials used in the overlay covering are not PSAs. They include, for example, a polyurethane film, foam or spun bonded structure, a polyolefin foam, a PVC foam or a woven or non-woven fabric. Illustrative wovens include KOB 051, 053 and 055 woven polyesters (Karl Otto Braun.) Illustrative non-woven fabrics include polyesters. An illustrative polyurethane material is CoTran™ 9700 melt-blown polyurethane nonwoven backing (3M), which can be colored in skin tones. Suitable materials are described, e.g., as backing layers in U.S. Pat. No. 6,660,295.

If the overlay covering is not porous, then it can be used without an intermediate layer. However, if the overlay covering is not porous, adhesion problems can result from a build up of moisture in the skin/PIB PSA interface. Use of a solid material, i.e., one that is not porous, but that is otherwise permeable to water, such as a thin, e.g., 1 mil (i.e., 0.001 inch), polyurethane film, can be used. However, a porous material such as a foam or fabric will, in general, better retain its shape and provide good adhesion.

Thus, based on the above description of an integrated transdermal delivery system, it can be seen that an aspect of this embodiment of the invention pertains to containing a volatile component in the AI layer by forming a seal between an overlay and a release liner.

Another aspect of this embodiment of the invention pertains to use of a PIB PSA in an overlay for an AI layer that comprises a volatile solvent, especially, DMSO, because DMSO is poorly soluble in PIB PSAs. See Table 1, below, which compares the solubility of DMSO in a polyacrylate PSA (Duro Tak 87-4098, National Starch) and in a PIB PSA such as is described above.

TABLE 1

| SATURATION SOLUBILITIES (MG/G) | | | |
|---|---|---|---|
| PSA | DMSO | Ethyl Lactate | Lauryl Lactate |
| Duro-Tak 87-4098 | 8 | 150 | 1000 |
| PIB PSA | 0.01 | 0.03 | 785 |

These data indicate that DMSO and ethyl lactate, which are both volatile, cannot migrate into the PIB PSA because of saturation considerations. Of course, it will be understood that some amount of absorption into the overlay is acceptable and, indeed, unavoidable, at least under certain conditions. It is important, however, in this embodiment of the invention, that the solubility of the volatile component in the AI containing layer be higher than, preferably substantially higher than, the solubility of the volatile component in the overlay PSA. References herein to a PSA that does not absorb volatile components must be understood in this context. In any event, the above data also indicate that the lauryl lactate, which is relatively not volatile, can flow into the PIB PSA by contact, which is why an internal backing layer is preferred in the transdermal drug delivery system of the invention.

Consistent with the above data, wear studies have shown that the PIB PSA retains its adhesiveness better than the polyacrylate PSA when stored in the presence of volatile enhancers owing to the reduced tendency of the volatile enhancers to migrate into the PIB PSA from an acrylic adhesive AI matrix, which migration would adversely affect the PIB PSA adhesiveness.

Overlay PIB and polyacrylate PSAs were tested in wear studies to determine their ability to adhere to skin for long periods of time. Table 2 shows that when absorption of excipients was minimized (25 C exposure) the acrylic adhesive gave better results than the PIB. When absorption of excipients was allowed to proceed in a more rapid rate (40 C exposure) the adhesion provided by the PIB PSA was better than that of the acrylic PSA. It is important to note that the adhesivity of the PIB PSA was the same when exposed to higher (40 C) or lower (25 C) conditions, for absorption of volatile excipients.

TABLE 2

ADHESIVITY OF INTEGRAL OVERLAY/ACTIVE PATCHES

| Overlay Adhesive | Equilibration Time | Equilibration Temperature | Adhesivity (1) |
|---|---|---|---|
| Acrylic | 1 month | 25 C. | 16.2 |
| Acrylic | 1 month | 40 C. | 12.8 |
| PIB | 1 month | 25 C. | 15.1 |
| PIB | 1 month | 40 C. | 15.1 |

(1) Note:
These are relative values in which a higher number signifies better adhesion.

Another aspect of this embodiment of the invention pertains to use of an overlay covering to cover the PIB PSA, which layer protects against contact with the PIB PSA and allows water vapor transmission. Another aspect of this embodiment of the invention pertains to use of a porous overlay covering and an intermediate layer that is permeable to moisture but that inhibits or prevents flow of the PIB PSA into and through the overlay covering.

The data in Table 3, below, illustrate that (1) use of a urethane overlay with or without a PIB PSA layer (PIB PSA is protecting the urethane on one side only) will result in absorption, and therefore loss, of volatile components such as are in the skin permeation enhancer composition illustrated in Examples 1 and 2 and (2) a polyester film does not absorb such components, even when coated with a PIB PSA such as when the internal backing layer is Mylar® and the overlay comprises a PIB PSA.

TABLE 3

ABSORPTION OF ENHANCERS BY PATCH COMPONENTS (wt %)

| 1. Polyurethane spun bonded nonwoven for overlay | CoTran(TM) 9700 (3M) | 10.6 |
|---|---|---|
| 2. Same as 1 but coated with acrylic adhesive | Hi-Tack Nonwoven Medical Tape 9904 (3M) | 9.65 |
| 3. Same as 2 but overcoated with 2 mm of PIB PSA (similar to Table 1) | | 7.6 |
| Polyester internal backing layer | Mylar® | 0.96 |
| Polyester coated with 2 mm PIB PSA (similar to Table 1) | Mylar® | 1.12 |

The data in Table 3 were obtained by placing in a metal dessicator the 4 enhancers in the same ratio as in the patch described in the Examples, below. The different components of the patch were placed in the same dessicator, making certain that the liquid enhancers (which were placed in a beaker on the bottom of the dessicator) were not in contact with the patch components. Therefore, any absorption of the enhancers into the patch components could only take place through vapor transfer. The dessicator was placed in a 40 C oven and the absorption into the patch components was measured by weighing the samples and determining the weight gain after 3 months.

Polyester non-woven fabrics, e.g., KOB 053 and KOB 055, were also shown not to absorb the volatile components to a significant extent.

EXAMPLES

The following examples are set forth to describe this embodiment of the invention in greater detail. They are intended to illustrate, not to limit, the invention.

Example 1

Fabrication of Transdermal Drug Delivery System

Example 1 is a description of one of the ways to fabricate a dermal delivery system of the invention. It will be appreciated that other ways can also be used. In this example, Part A illustrates preparation of Internal Backing/AI layer/Release Liner Laminate. Part B illustrates fabrication of a foam/acrylic PSA/PIB PSA overlay structure. Part C illustrates fabrication of an integrated device, or system, of the invention utilizing the laminates prepared in Parts A and B.

Part A. Fabrication of an Internal Backing/AT layer/Release Liner Laminate: After deaeration, an adhesive polymer composition comprising the AI and the volatile component(s) is applied to the backing layer material, and subsequently dried for a set time at a set temperature. In an alternative embodiment, the adhesive polymer matrix may be applied to a release liner instead of to the backing layer. Accordingly, reference herein to application of the adhesive polymer matrix to the backing layer will be understood to include this alternative embodiment. Application of the deaerated adhesive polymer matrix to the backing layer may be accomplished using commercially available laboratory coating/drying apparatus routinely used for this purpose. For instance, the Werner Mathis Model LTSV/LTH apparatus may be utilized, as well as other laboratory coating devices available from Werner Mathis AG (Zurich, Switzerland). Other suitable devices include, but are not limited to, instruments produced by Chemsultants, Inc. (Mentor, Ohio).

The thickness of the adhesive polymer solution applied to the backing layer, as well as the time and temperature of drying, are all process parameters that can be varied to achieve the final concentrations and ratios of hormones and permeation enhancing agents within the patch. For instance, it has been found that a change in the thickness of adhesive polymer matrix applied to the backing layer (e.g., from 300 to 800 µm) can result in an overall greater retention of volatile skin permeation enhancers when the other two process parameters, drying time and drying temperature, are held constant. In contrast, changing the drying time, e.g., from 5 to 25 minutes, or the drying temperature, e.g., from 40-100 C, can result in overall losses in retention of volatile skin permeation enhancers, to a greater or lesser degree depending on the enhancer.

Thus, it will be appreciated by those of skill in the art that, in addition to selection of appropriate amounts of starting materials in the adhesive polymer starting formulation, an appropriate combination of (1) initial thickness of the deaerated adhesive polymer solution spread on the backing layer, (2) drying time and (3) drying temperature may be selected to achieve the final composition of skin permeation enhancers and AIs in the device.

The dried adhesive polymer matrix is next laminated with a piece of release liner (such as Scotchpak® 1022 or 9744, 3M Co., St. Paul Minn.) (or backing layer, if the alternative embodiment is utilized), preferably of the same size to form a sheet of the transdermal hormone delivery systems.

Part B. Fabrication of a Non-Woven/Acrylic PSA/PIB PSA Overlay Laminate: The Fabrication of the Overlay is Performed in Two Steps.

In the first step, a PET-silicone coated release liner is unwound and a solution of an acrylic adhesive Duro-Tak 87-2852 is coated on the silicone side of the release liner. The web proceeds through heated ovens where the solvents are blown off and the release liner/solid acrylic PSA laminate is formed. The laminate proceeds toward a laminator unit where the 3M 9700 spun bonded non-woven is unwound and the acrylic PSA and the 3M 9700 go through the heated laminator rolls where a three layer laminate is formed (3m 9700/acrylic PSA/silicone release liner).

In the second step a PET-silicone coated release liner is unwound and a solution of a PIB PSA is coated on the silicone side of the release liner. The web proceeds through heated rolls where the solvents are blown off and the release liner/solid PIB PSA laminate is formed. The laminate proceeds toward a laminator unit where the 3M 9700/acrylic PSA/silicone release liner laminate is positioned. The 3M 9700 laminate is unwound, its release liner is removed and discarded and the rest of the laminate proceeds toward the heated laminator rolls where it combines and gets laminated to the release liner/solid PIB PSA laminate to form the finished overlay composed of 3M 9700 spun bonded non-woven/acrylic PSA/PIB PSA/silicone release liner.

Part C. Fabrication of an Integrated Device of the Invention (Double Disc Conversion Process):

The conversion of a double disc, peripheral adhesive transdermal delivery device is fabricated on a die cutting-laminating piece of equipment typical for the industry. It has at least two payout stations, two die cutting stations, one lamination station, and three rewind stations. A roll of overlay laminate (Polyurethane, Polyacrylate PSA and PIB PSA) from Part B and a roll of release liner/active patch/internal backing layer laminate from Part A are mounted onto the payout spindles. The active patch laminate is threaded through a die cutting station where a partial or kiss cut is performed in the shape of the active patch through the internal backing and AI layer, and not through the release liner. The waste material around the patches is delaminated from the protective liner and wound onto a rewind spindle.

The overlay laminate is threaded through the conversion machine, the release liner is removed and the exposed overlay adhesive-urethane backing is laminated over the patch and onto the release liner from the active patch laminate. The resultant laminate with the active patch sandwiched between the overlay and the release liner is die cut in a shape larger than the active patch and collected for the next processing step. The resulting liner with holes cut out in the shape of the overlay-patch is wound on a rewind spindle.

Example 2

Control of Loss of Volatile Components

A transdermal hormone delivery device was prepared comprising an internal backing layer, an AI layer, and a release liner. The AI layer comprised, as a polymer matrix PSA: Duro Tak 87-4098; as a humectant: PVP/VA-S360; as skin permeation enhancers: dimethylsulfoxide (DMSO), lauryl lactate (Ceraphyl® 31), ethyl lactate, and capric acid; as the AI: levonorgestrel and ethinyl estradiol.

The device also comprised an overlay comprising a polyurethane spun bonded non-woven backing, which is able to absorb large amounts of the volatile excipients, DMSO and ethyl lactate, an acrylic PSA coated onto the polyurethane foam, and a PIB PSA coated on top of the acrylic PSA. The internal backing layer was composed of a Mylar polyester backing film onto which was coated an acrylic PSA containing the AI as well as the volatile excipients, DMSO and ethyl lactate at 8 wt % and 1.7 wt % nominal concentrations, respectively, and a non-volatile excipient, lauryl lactate at 8.4 wt % nominal concentration. The release liner was a Mylar polyester film coated with a fluoropolymer release coating. The patches were assembled so that the release liner was in direct contact with the PIB PSA of the overlay, forming an in situ seal around the active patch.

The devices were placed in a 25 C or 40 C oven. After 6 weeks and 12 weeks, devices were removed from the oven and the active section of each device was separated from the overlay. The amounts of DMSO, lauryl lactate, and ethyl lactate in the active patch were determined using gas chromatography. (12 weeks exposure to 40 C is intended to simulate 18 months exposure to room temperature (25 C)). The results are shown in Table 4.

TABLE 4

Amounts of DMSO, Ethyl Lactate, and Lauryl Lactate in the AI Patch

| Conditions | DMSO (wt %) | Ethyl Lactate (wt %) | Lauryl Lactate (wt %) |
|---|---|---|---|
| 6 wks, 40 C. | 9.02 | 1.66 | 9.02 |
| 12 wks, 40 C. | 8.98 | 1.57 | 9.20 |
| 12 wks, room temp | 9.08 | 1.79 | 9.10 |

These results demonstrate that the seal between the overlay and the release liner and the use of an overlay, internal backing layer, and release liner, are adequate to prevent loss of volatile components (DMSO, ethyl lactate) and a non-volatile component (lauryl lactate).

Dermal delivery devices of the invention can optionally be packaged for distribution and sale to users. Standard packaging can be used or, if desired, packaging that exerts pressure on the in situ seal between the release liner and the PSA of the overlay can be employed. The purpose for such packaging is to keep the release liner and overlay in contact with each other and to minimize slippage or gapping that might occur, e.g., during transportation. Such packaging can comprise a closable packet (e.g., a clamshell packet that is hinged to open but that can be snapped close) that when closed fits snugly around the perimeter of the delivery device, thereby exerting a small amount of pressure on the in situ seal, but that is shaped so as not to squeeze the AI-containing patch.

Example 3

Clinical Study

Devices of a type described in Example 2 were analyzed for adhesion and irritation in a clinical study. Placebo patches or patches containing actives were applied to the skin of women for pre-determined time periods, among which were (1) one week, (2) two monthly treatment cycles, and (3) three monthly treatment cycles.

Adhesion Analyses:

A) Placebo patches applied for one week to 59 women: one out of 59 patches (1.7%) exhibited meaningful degree of detachment;

B) Active patches applied for two treatment cycles to 38 women: 12 out of 149 patches (8.1%) exhibited meaningful degree of detachment;
C) Placebo and active patches applied for three treatment cycles to 59 women: 13 out of 208 patches (6.3%) exhibited meaningful degree of detachment;

The mean cumulative total adhesion score (calculated per FDA Guidance) was 0.9 with an upper limit of 1.38 (placebo patch, one week, 59 women).

Irritation Analyses:
A) Placebo patches applied for one week to 54 women: 0 out of 54 patches (0.0%) resulted in significant irritation and 1 out of 54 patches (1.9%) resulted in moderate irritation.
B) Active patches applied for two treatment cycles to 38 women: 0 out of 143 patches (0.0%) resulted in significant irritation and 6 out of 143 patches (4.2%) resulted in moderate irritation.
C) Placebo and active patches applied for two treatment cycles to 54 women: 0 out of 197 patches (0.0%) resulted in significant irritation and 7 out of 197 patches (3.6%) resulted in moderate irritation.

The mean cumulative total irritation score (calculated per FDA Guidance) was 0.11 with an upper limit of 0.21 (placebo patch, one week, 54 women).

The present invention is not limited to the embodiments described and exemplified above, but is capable of variation and modification within the scope of the appended claims. Published patent applications and patents referenced in this specification are incorporated herein by reference as though fully set forth.

The invention claimed is:

1. A non-heat sealed transdermal drug delivery device that comprises:
   (a) a polymer matrix active ingredient (AI) layer having a skin-contacting surface and a non-skin contacting surface; the AI layer comprising an active ingredient, a pressure sensitive adhesive (PSA), and at least one volatile component which is at least partly solubilized in the PSA of the AI layer;
   (b) a release liner in direct contact with the skin-contacting surface of the AI layer, the perimeter of which extends beyond the perimeter of the AI layer in all directions;
   (c) an overlay adjacent to the non-skin contacting surface of the AI layer, the perimeter of which extends beyond the perimeter of the AI layer in all directions; the overlay comprising:
      (i) a PSA layer; and
      (ii) an overlay covering; and
   (d) an internal backing layer between the AI layer and the overlay;
   in which device:
   the PSA of the Al layer is a polyacrylate PSA;
   the volatile component comprises DMSO, ethyl lactate, or both;
   the PSA layer of the overlay is a polyisobutylene (PIB) PSA, a silicone PSA, a styrene/butadiene/styrene PSA, styrene/isoprene/styrene PSA, a styrene-ethylene/butylene-styrene PSA, a styrene/butadiene PSA, a styrene-ethylene/butylene-styrene PSA, a styrene-ethylene/propylene-styrene PSA or an isoprene rubber PSA;
   the release liner and the PSA layer of the overlay are in direct contact with and adhered to each other around the perimeter of the Al layer to form a PSA seal between the overlay and the release liner;
   the solubility of the volatile component in the PSA of the PSA layer of the overlay is less than the solubility of the volatile component in the PSA of the AI layer such that the PSA seal between the overlay and the release liner reduces or prevents loss of the at least one volatile component from the Al layer; and
   the overlay covering is non-tacky, flexible, and moisture permeable;
   whereby at the end of an extended wear period, the patch causes cumulative moderate irritation plus significant irritation of less than 5% or exhibits meaningful degree of detachment over a seven day wear period of less than 20%, or both.

2. The device of claim 1, wherein the polyacrylate PSA of the AI layer is a polyacrylate adhesive copolymer having a 2-ethylhexyl acrylate monomer and 50 to 60 wt% vinyl acetate as co-monomer.

3. The device of claim 1, wherein the release liner comprises a fluorinated or siliconized polymer film, or a foil lined with a siliconized or fluorinated polymer.

4. The device of claim 1, wherein the PSA layer of the overlay comprises a silicone PSA.

5. The device of claim 1, wherein the PSA layer of the overlay comprises a PIB PSA and in which the overlay further comprises a polymeric intermediate layer comprising a polyacrylate PSA.

* * * * *